United States Patent
Kam et al.

(10) Patent No.: US 8,449,553 B2
(45) Date of Patent: May 28, 2013

(54) METHOD OF USING A DRILL GUIDE FOR FORMING TIBIAL BONE TUNNELS

(75) Inventors: Andrew Kam, Odessa, FL (US); Hugh S. West, Sandy, UT (US)

(73) Assignee: Linvatec Corporation, Largo, FL (US)

( * ) Notice: Subject to any disclaimer, the term of this patent is extended or adjusted under 35 U.S.C. 154(b) by 0 days.

(21) Appl. No.: 13/374,723

(22) Filed: Mar. 20, 2012

(65) Prior Publication Data

US 2012/0239044 A1 Sep. 20, 2012

Related U.S. Application Data

(62) Division of application No. 12/315,408, filed on Dec. 3, 2008, now abandoned.

(51) Int. Cl.
*A61B 17/17* (2006.01)
(52) U.S. Cl.
USPC ............................................. 606/96; 606/88
(58) Field of Classification Search
USPC .................... 606/79, 80, 88, 96, 98; 623/902, 623/908
See application file for complete search history.

(56) References Cited

U.S. PATENT DOCUMENTS

| 2002/0095214 A1* | 7/2002 | Hyde, Jr. ........................ 606/80 |
| 2003/0135215 A1* | 7/2003 | Leali .............................. 606/72 |
| 2009/0143784 A1* | 6/2009 | Petersen et al. ................ 606/96 |
| 2009/0149858 A1* | 6/2009 | Fanelli et al. .................. 606/80 |

* cited by examiner

*Primary Examiner* — Brian E. Pellegrino
(74) *Attorney, Agent, or Firm* — Gene Warzecha (57) ABSTRACT

A guide that facilitates the creation of two bone tunnels for use during a "double bundle" cruciate ligament repair. In the case of an anterior cruciate ligament repair the guide facilitates the formation of two tibial tunnels extending between a single aperture on the anterior tibia and two distinct apertures on the tibial plateau. The guide has a single angled through-bore for guiding a drill bit on a predetermined angle relative to the anterior portion of the tibial tunnel. In an alternative embodiment the guide has two independent and non-intersecting bores which allow the simultaneous placement into the tibial tunnel of two separate guide pins to guide the formation of two tibial tunnels on the tibial plateau.

1 Claim, 8 Drawing Sheets

METHOD OF USING A DRILL GUIDE FOR FORMING TIBIAL BONE TUNNELS

This application is a divisional of application Ser. No. 12/315,408, filed Dec. 3, 2008 now abandoned.

BACKGROUND OF THE INVENTION

1. Field of the Invention

The invention relates to drill guides for guiding drills during surgical procedures. More particularly, this invention relates to drill guides for positioning drills during orthopedic surgical procedures. Still more particularly, this invention relates to drill guides for positioning drill bits during arthroscopic repair of anterior and posterior cruciate ligaments.

2. Description of the Prior Art

Drill guides for positioning drill bits during arthroscopic surgical procedures are well known. Generally, such drill guides comprise a generally C-shaped structure in which one end of the C is situated at a point on the tibial plateau, representing one end of a tibial bone tunnel, and another point at the other end of the C representing the entry point of the tibial tunnel. (An example of such a guide is shown in U.S. Pat. No. 5,154,720 (Trott et al.) assigned to the assignee hereof and incorporated herein.) Guiding structures are attached in order to enable a user to drill from one end of the C to the other to thereby create a bone tunnel which will ultimately be used to anchor one end of a graft replacement ligament.

Recently, cruciate ligament repair procedures have evolved into the use of a "double bundle" technique in order to more accurately approximate the anatomical structure of an original ACL. The prior art double bundle technique requires the formation of two bone tunnels in the tibia, one for each bundle of the replacement ligament graft, and two corresponding bone tunnels in the femur. The present invention relates to a guide for properly locating and forming two modified tibial bone tunnels.

It is accordingly an object of this invention to provide a double bundle tibial guide to accurately position the exit of both tibial bone tunnels on the tibial plateau.

It is another object of this invention to provide a guide to accurately position the exit of two bone tunnels on a selected bone surface.

It is yet another object of this invention to accurately position both tunnels relative to each other.

SUMMARY OF THE INVENTION

These and other objects of this invention are achieved by the preferred embodiment disclosed herein. In one aspect, the invention is a guide for guiding a drill bit into a preformed bone tunnel having a first diameter. The guide comprises an elongated body having a proximal end, a distal end, a first axis and a cylindrical portion at the distal end. The cylindrical portion is coaxial with the axis and has a predetermined outer diameter adapted to fit within the bone tunnel. The guide further comprises a bore which extends through the cylindrical portion, the bore having a second axis and being oriented at a predetermined angle relative to the first axis.

Another aspect of the invention is the method of creating a pair of tibial bone tunnels, each having a separate exit aperture on the tibial plateau. The method comprises the steps of forming a first bone tunnel extending from the anterior tibia toward but not through the tibial plateau, and providing a guide such as the aforementioned guide. The method further comprises the step of inserting the cylindrical distal portion of the guide into the bone tunnel, drilling through the distal portion of bone in the first bone tunnel to form a second bone tunnel having a predetermined diameter smaller than the diameter of the first bone tunnel, thereby producing a shoulder between the first and second bone tunnels, inserting the guide into the first bone tunnel, advancing the guide until it abuts the shoulder at the junction of the first and second bone tunnels, orienting the guide about its axis to align the bore with a selected point on the tibial plateau and advancing a drill through the bore toward the selected point on the tibial plateau to form a third bone tunnel.

DESCRIPTION OF THE PREFERRED EMBODIMENT

Figure 1:
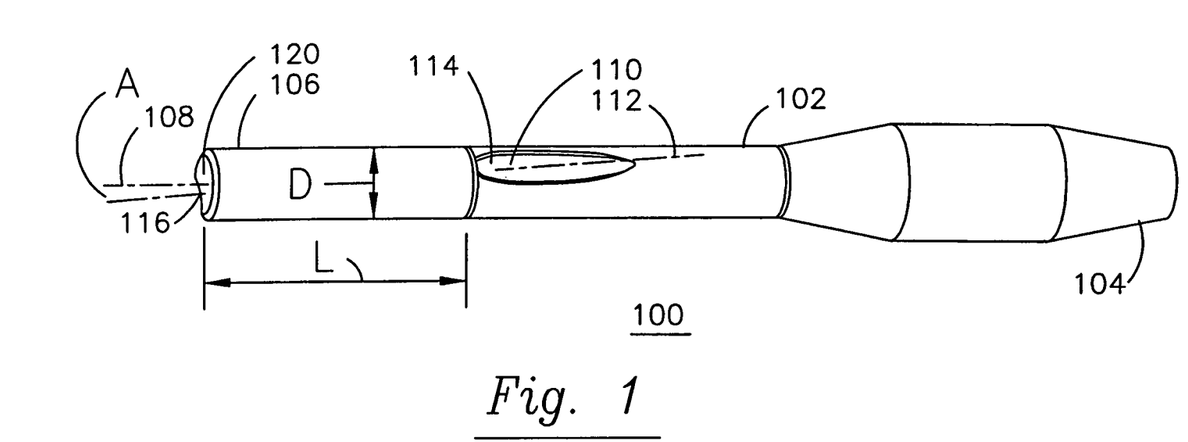
FIG. 1 is a perspective view of a guide constructed in accordance with the principles of this invention

As shown in FIG. 1, guide 100, constructed in accordance with the principles of this invention, comprises body 102 having a proximal end 104 and a distal end 106. Guide 100 has an axis 108 and a single inclined bore 110 having an axis 112 situated at an angle A relative to axis 108. Bore 110 extends between an entry point 114 on the side of body 102 and an exit point 116 coincident with transverse end surface 120 situated at the distal end 106. The distal end 106 is in the form of a cylinder having a diameter D and length L adapted to fit into a bone tunnel as will be understood below.

Figure 2:
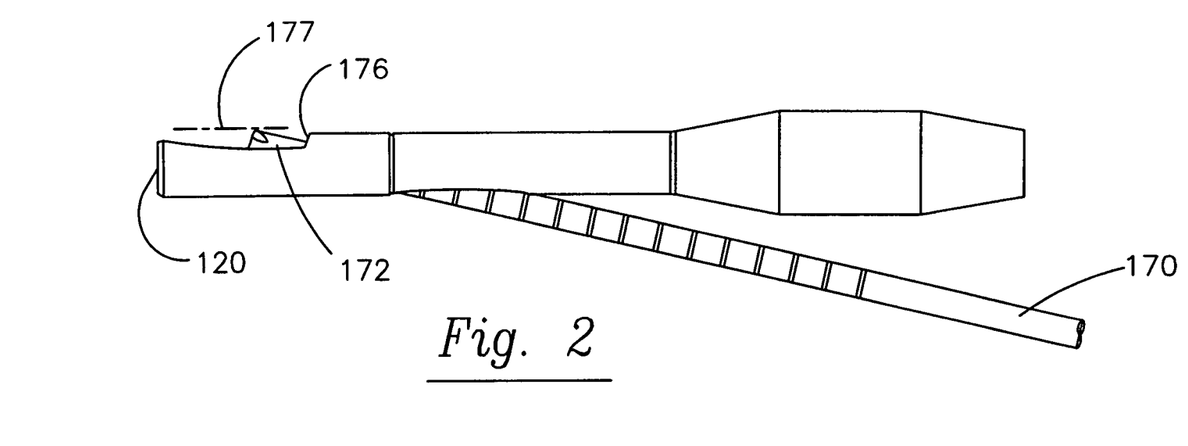
FIG. 2 is a side elevation view of the guide of FIG. 1 assembled with a drill bit.
Figure 3:
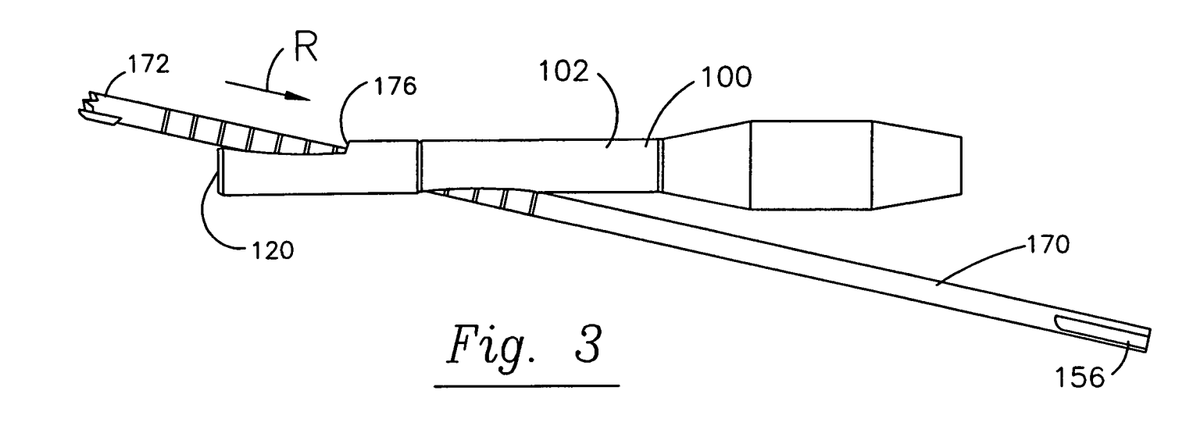
FIG. 3 is a view of FIG. 2 showing the drill bit in a different orientation relative to the guide.

Bore 110 has a diameter designed to receive an elongated drill bit 170 as seen in FIGS. 2 and 3. Drill bit 170 is slidable within bore 110 between a retracted position as shown in FIG. 2 and an advanced position as shown in FIG. 3.

The preferred embodiment of the device and method disclosed herein is intended primarily for use in the tibia to prepare two bone tunnels having spaced apart exit apertures on the tibial plateau and a single entrance aperture on the anterior tibia. However, it will be understood that guide 10 may be used in a variety of procedures to create two bone tunnels, particularly two tunnels having exit apertures spaced apart a predetermined distance on a selected (generally posterior or distal) bone surface. The device and method described below will facilitate the creation of a proximal bone tunnel (starting on a generally anterior or proximal bone surface) that splits into two distinct distal tunnels. The proximal bone tunnel is common to both of the distal tunnels and facilitates using a single interference screw to secure the grafts in both tunnels to the tibia.

The operation of guide 100 and the functions of its various features are best described in the context of an anterior cruciate ligament repair, particularly in the context of a double bundle repair. In a double bundle repair the surgeon prepares two tunnels in order to provide two separate tunnel exit apertures on the tibial plateau. Each tunnel receives a particular soft tissue graft ligament which is in effect attached to the tibia at points coincident with the spaced apart exit apertures.

Figure 4:
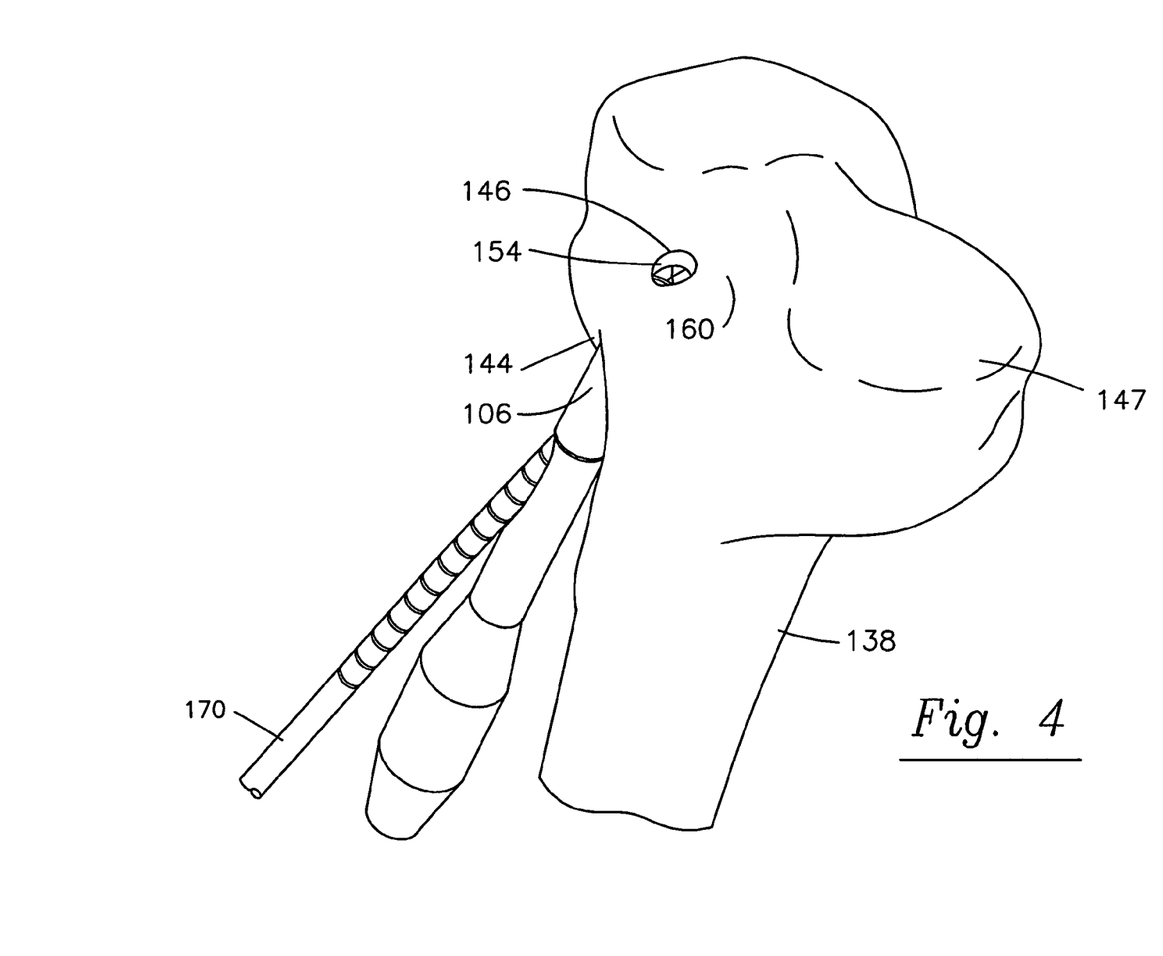
FIG. 4 is a view of the guide and drill bit within a bone tunnel in a tibia.
Figure 5:
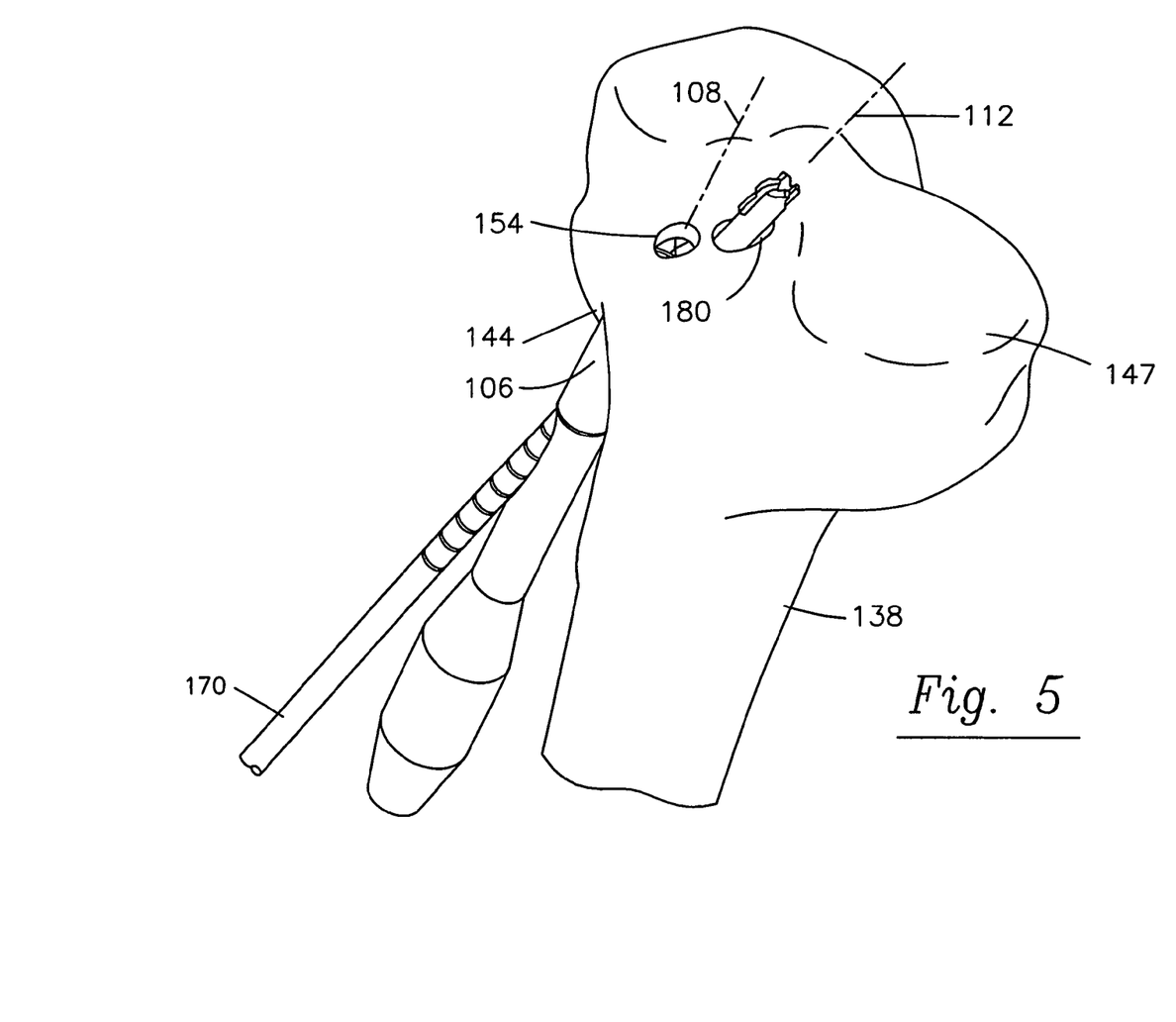
FIG. 5 is a view of the guide within a bone tunnel in a tibia and showing the drill bit advanced so as to form a second bone tunnel.
Figure 6:
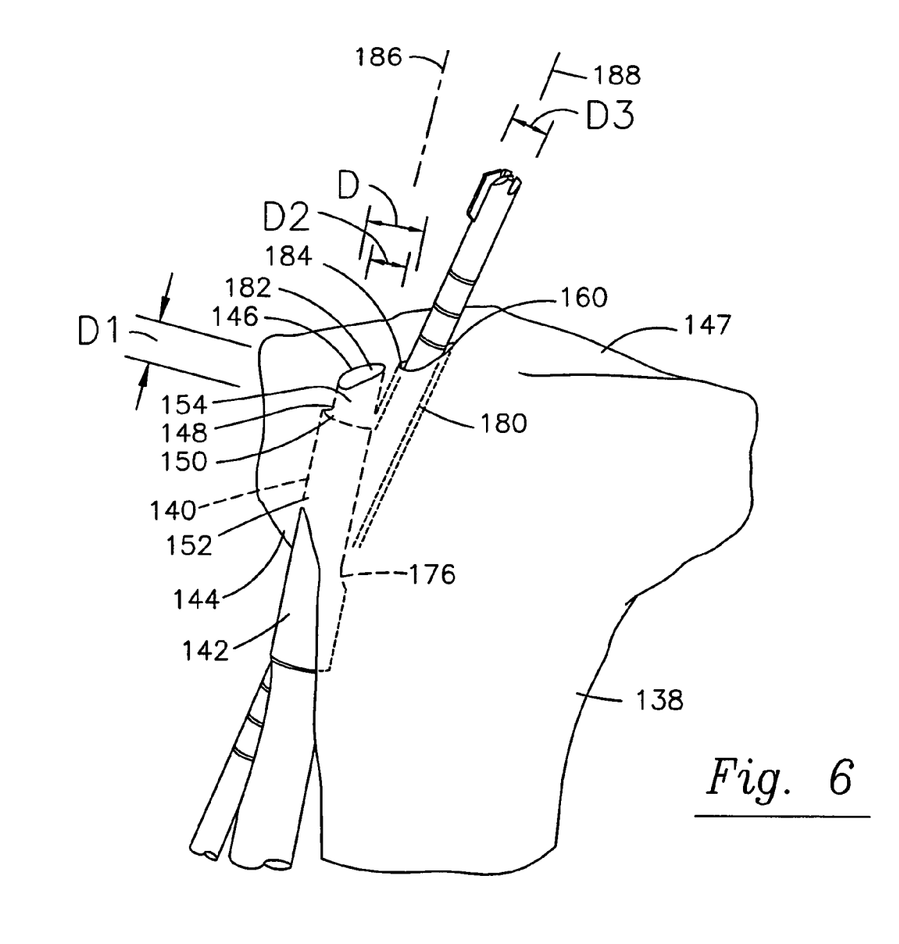
FIG. 6 is a view of FIG. 5 partially in cross-section.

As best seen in FIGS. 4 through 6, the double bundle technique of this invention begins with the partial formation of a single proximal bone tunnel in a tibia 138 utilizing a conventional tibial guide (not shown) to create a bone tunnel 140. In the preferred embodiment, bone tunnel 140 (sometimes referred to herein as a first bone tunnel) is formed by using a guide pin (not shown) in conjunction with the aforementioned prior art tibial guide (not shown) to guide the guide pin from a point 142 on the anterior tibia 144 toward a point 146 on the tibial plateau 147. Once the guide pin pierces the tibial plateau a first cannulated drill bit (not shown) having a diameter D is guided along the guide pin to create proximal bone tunnel 140 to within a predetermined distance D1 of the tibial plateau, such distance preferably being on the order of 10 mm, thereby leaving a thin portion of bone 148 covering bone tunnel 140. At this point in the procedure the first cannulated drill bit is removed, leaving the guide pin, and a second cannulated drill bit is selected to follow along the guide pin to continue through the thin portion of bone 148. The second drill bit has a diameter D2 which is less than diameter D such that a ledge or shoulder 150 is created in bone tunnel 140 between proximal tunnel portion 152, having a diameter D, and distal tunnel portion 154 (sometimes referred to herein as the second bone tunnel), having a diameter D2, best seen in FIGS. 4 and 6. Shoulder 150 provides a fixed reference point for the formation of the second tunnel as will be understood below. Diameter D2 is equal to the diameter of the particular bundle which will ultimately be received within distal bone tunnel portion 154. At this point the second drill bit and the guide pin are removed.

For a double bundle procedure, of the two tunnels required one is anterior on the tibial surface and the other is generally posterior thereto. Both tunnels may have different diameters corresponding to the size of the particular graft ligament bundle to be received in its respective tunnel. Distal tunnel portion 154 is the anterior one in this explanation. Guide 100 is now used to create the posterior tunnel.

When the diameter of the posterior graft ligament bundle is determined, a third drill bit 170 having a diameter D3 equal to that of the posterior bundle is inserted into bore 110 of guide 100 in retrograde fashion as best seen in FIG. 3. That is, in the preferred embodiment the diameter of the shaft of drill bit 170 is smaller than the diameter of its head 172 and the diameter of bore 110 within body 102 is sized to accommodate the shaft. This enables tighter control over drill 170. By assembling drill 170 into guide 100 in retrograde fashion (in direction R) the drill head 172 will ultimately abut the exit point (shoulder) 176 of bore 110. From point 176 distally toward the end 120 of guide 100 bore 110 has a diameter equal to or slightly greater than diameter D3, in order to accommodate head 172. Drill bit 170 and guide 100 are assembled so that the head 172 of drill bit 170 is retracted into bore 110 such that no portion of the head 172 extends beyond the lateral extent 177 of body 102 at point 176 where it intersects with the exit of bore 110. This last point enables the assembled drill bit and drill guide to be inserted into proximal bone tunnel 140 through the single anterior aperture 142 as shown in FIG. 4.

The cylindrical distal end 106 of drill guide 100 is inserted into bone tunnel 140 until its distal end surface 120 abuts against the shoulder 150 at the juncture of proximal tunnel portion 152 and distal tunnel portion 154. Guide 100 is then oriented in a selected rotary position around axis 108 in order to aim axis 112 at a suitable exit point 160 on the tibial plateau. An index mark is situated on the surface of body 102 to facilitate aiming axis 112. Point 160 is intended to be generally posterior of point 146 and is intended to be the exit aperture for the second of the two tunnels to be formed. Drill bit 170 is cannulated, allowing a guide pin (not shown) to be drilled through the cannulation of drill bit 170 to point 160. Should the location need to be changed, the pin may be removed and the guide may be repositioned before posterior tunnel 180 (sometimes referred to herein as the third tunnel) is formed. Once the proper guide orientation is selected, the drill bit 170 may simply follow the guide pin to exit the tibial plateau at the selected point.

It is preferable during this procedure to use a drill bit 170 having a monofluted, circumferentially asymmetric head 172 similar to that manufactured by ConMed Linvatec under the trademark SENTINEL®. Alternatively, depending upon the chosen dimensions of the drill bit head and the guide bore 110, a conventional drill bit with a circumferentially symmetric head may be used. Once both anterior and posterior tunnels 154 and 180 have been formed, the guide pin drill bit and guide may all be removed to allow the procedure to continue.

Bone tunnel 140 comprises a proximal tunnel portion 152 which is a single cylindrical tunnel having a single axis and intersecting the anterior tibia at a single aperture 142. Bone tunnel 140 also comprises an anterior distal tunnel portion 154 and a posterior distal tunnel 180, each tunnel intersecting the tibial plateau 147 at their distal-most exit apertures 182 and 184, respectively. Tunnel exit apertures 182 and 184 are aligned with their axes 186 and 188, respectively, in a common plane extending generally anterior to posterior.

It will be understood that the axes 186 and 188 are spaced apart along the tibial plateau by a predetermined distance sufficient to effect the purposes of the double bundle techniques. Each distal tunnel section 154 and 180 receives a particular bundle of a graft ligament, and both handles are together received in the common proximal tunnel section 152. The spacing along the tibial plateau may be selected by using a guide 100 that is dimensioned, primarily by variation in the angle A between axes 108 and 112, to produce a different spacing.

It is noted that length L of distal end 106 is sufficiently long to enable bore 110 to receive a drill bit such that the proximal end is accessible from a point outside the anterior tibia without interference from the tibial tunnel wall.

Figure 7:
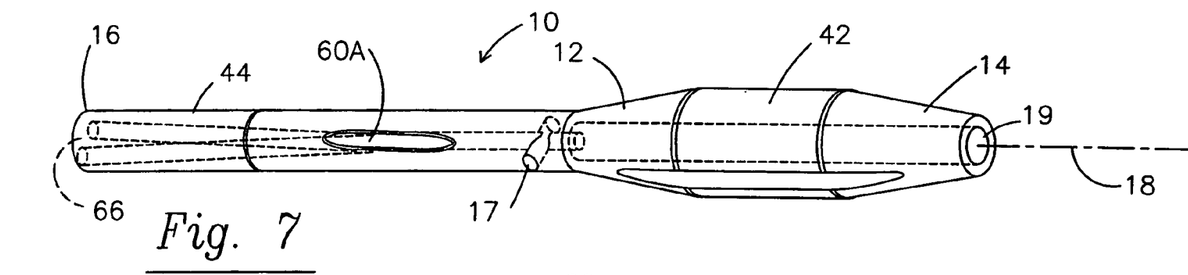
FIG. 7 is a perspective view of an alternate embodiment of the guide.

An alternative embodiment of the tibial guide of this invention comprises guide 10, best seen in FIG. 7. Guide 10 is used with a single tibial tunnel similar to tunnel 140 shown in FIG. 6. Guide 10 comprises a body 12 having a proximal end 14, a distal end 16 and an axis 18. An axial bore 19 extends along the length of body 12. Guide 10 is used to guide two guide pins 50 and 52, best seen in FIGS. 8 and 9. (In FIGS. 8 and 9 the end of bore 19 at the distal end 16 is omitted for clarity.)

Guide 10 has a handle 42 and a tunnel engaging cylindrical distal portion 44. Distal portion 44 is inserted into a single tibial tunnel following an axially aligned guide pin (not shown) after the tunnel has been formed by conventional means as discussed above. Once the single tunnel (like tunnel 140 of FIG. 6) has been formed by drilling over the guide pin, the drill is removed so guide 10 can be placed on the guide pin via bore 19. Two diametrically opposed indicia 17 on handle 42 indicate how guide 10 should be aligned to assure anterior-posterior positioning of guide pins 50 and 52 ultimately used to form the "double bundle" tunnels. Each indicia 17 shows the orientation of a respective guide pin bore at the distal end of guide 10.

Figure 14:
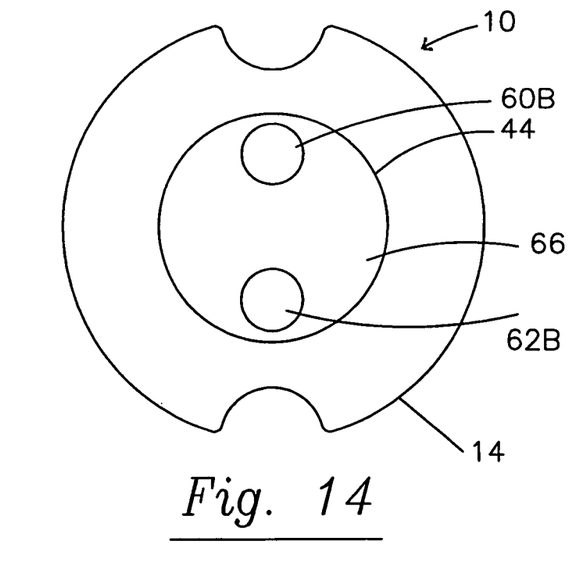
FIG. 14 is a left end view of FIG. 13 showing the exit apertures of both guide bores.

In order to form the "double bundle" tunnels, guide 10 comprises two independent, non-intersecting bores 60 and 62 best seen in FIGS. 10-13. Each of these bores has an entrance aperture 60A and 62A, respectively, on the surface of body 12 at points proximal to tunnel engaging distal portion 44. This enables guide pins 50, 52 to be inserted into bores 60 and 62, respectively, while distal portion 44 is in the tibial tunnel. Bores 60 and 62 are both situated within body 12, however, for clarity, only a single bore is shown in each of FIGS. 10-13. As shown in FIG. 14, each bore 60 and 62 has an exit aperture 60B and 62B, respectively, on the distally facing surface 66 of distal end 16. The exit apertures are aligned in a generally anterior-posterior plane. (It will be understood that FIG. 14 also includes an axial aperture, representing the distal end of bore 19, although this has been omitted for clarity.)

It will be understood that the inclination of guide pins 50 and 52 relative to axis 18 will cause the pins to be separated by a distance D4 (lateral view) that is greater than the diameter D5 of distal portion 44. Thus, the spacing of the exit apertures of the two tunnels on the tibial plateau depends on the distance of the tibial plateau from the distal end of the single tibial tunnel (and, therefore, it depends on the thickness of the thin bone layer 148 of FIG. 6).

After the guide pins 50, 52 are set in the bone distal to the single tibial tunnel, the guide 10 may simply be pulled out of the tunnel (in part because of the flexibility of the pins), leaving the guide pins in place to guide drill bits to form each of the "double-bundle" tunnels.

Figures 8, 9:
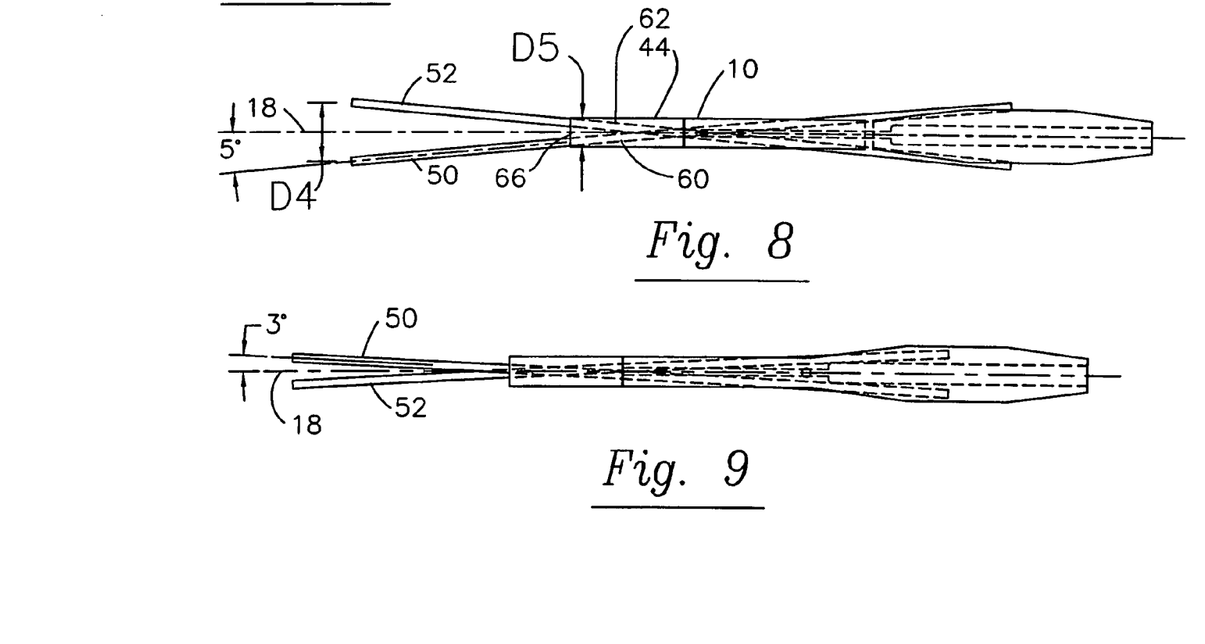
FIG. 8 is a side elevation view of the guide of FIG. 7 assembled with two guide pins.
FIG. 9 is a top plan view of FIG. 8.
Figure 10:
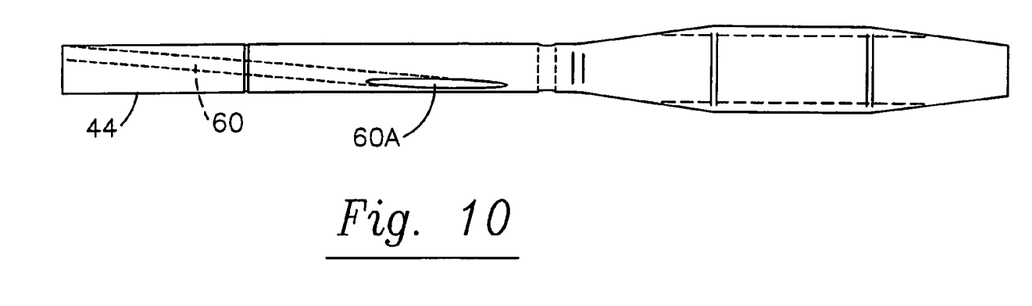
FIG. 10 is a side elevation view, partially in cross-section, showing only one of two guide bores for clarity.
Figure 11:
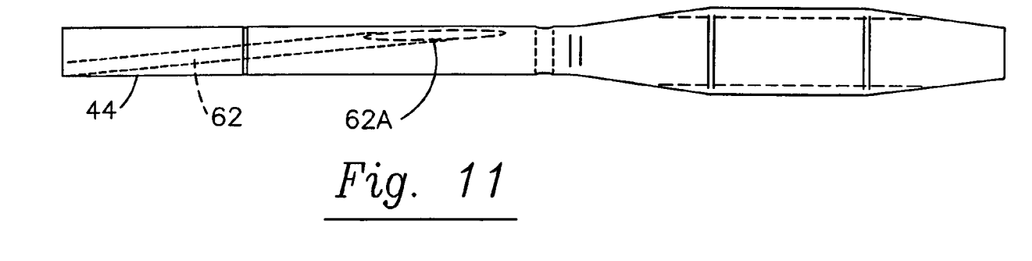
FIG. 11 is a view of FIG. 10 showing the other of the two guide bores.
Figure 12:
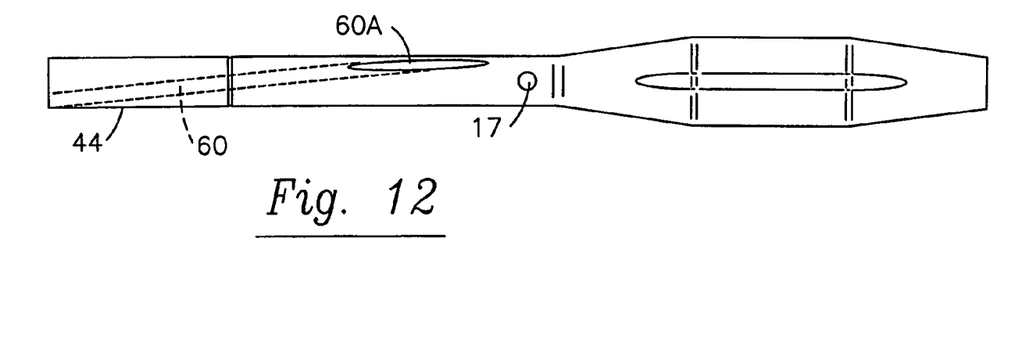
FIG. 12 is a bottom plan view of FIG. 10 showing the guide bore thereof from a different perspective.
Figure 13:
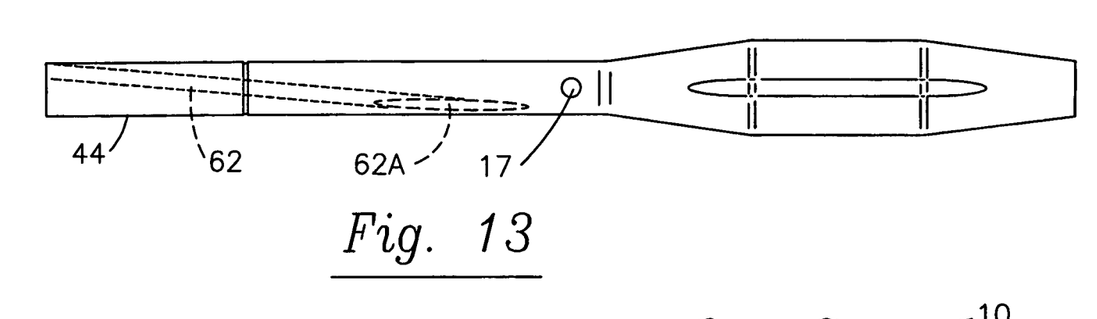
FIG. 13 is a bottom plan view of FIG. 10 showing the other of the two guide bores.

As shown in FIGS. 8 and 9, the guide pin cannulations 60 and 62 are inclined relative to the axis 18 of the guide 10. When seen in an anterior-posterior view (FIG. 9) the cannulations 60 and 62 do not intersect the axis of the guide and are angled relative to each other by an angle on the order of 6°. In this A/P view the guide pins passing through these cannulations are aligned in planes which are angled relative to axis 18 by an angle on the order of 3°. When viewed in the lateral view (FIG. 8), the guide pin cannulations are aligned in planes angled relative to axis 18 by an angle on the order of 5° and angled relative to each other by an angle on the order of 10°.

The intent of guide 10 is to produce two tunnel exit apertures on the surface of the tibial plateau in such a way that the two exit apertures are aligned within the same plane as the axis of the guide. Furthermore, the goal is to produce these two exit apertures with one instrument (the guide) which does not need to be moved until the formation of both tunnels is complete. In addition, the formation of the tunnels does not need to begin until the locations of both tunnels are identified so the surgeon does not need to commit to the location of any tunnel until he or she is satisfied with the location of both tunnels. To accomplish this, guide 10 enables the alignment of two graft pins, one for each tunnel, simultaneously through the same guide body.

It will be understood by those skilled in the art that numerous improvements and modifications may be made to the preferred embodiment of the invention disclosed herein without departing from the spirit and scope thereof.

What is claimed is:

1. A method of creating a pair of tibial bone tunnels, each having a separate exit aperture on the tibial plateau, said method comprising the steps of:

forming a first common bone tunnel extending from the anterior tibia toward but not through the tibial plateau, thereby leaving a thin bone portion between the tibial plateau and the end of said first common bone tunnel;

providing a guide for guiding a drill bit into said first common bone tunnel, said first common bone tunnel having a first diameter, said guide comprising:

an elongated body having a proximal end, a distal end, a first axis and a cylindrical portion at said distal end, said cylindrical portion coaxial with said axis and having a predetermined outer diameter adapted to fit within said first common bone tunnel;

a bore extending through said cylindrical portion, said bore having a second axis, oriented at a predetermined angle relative to said first axis, inserting the cylindrical distal portion of said guide into said first common bone tunnel;

drilling through said thin bone portion of bone at the end of said first common bone tunnel to form a second bone tunnel in communication with said first common bone tunnel, said second bone tunnel having a predetermined diameter smaller than the diameter of said first common bone tunnel, thereby producing a shoulder between said first common bone tunnel and said second bone tunnel;

advancing said guide until it abuts the shoulder at the junction of said first common bone tunnel and said second bone tunnel;

orienting said guide about its axis to align said bore with a selected point on the tibial plateau;

advancing a drill through said bore toward said selected point on the tibial plateau to form a third bone tunnel in communication with said first common bone tunnel.

* * * * *